(12) United States Patent
Nowaczyk

(10) Patent No.: US 7,168,142 B2
(45) Date of Patent: Jan. 30, 2007

(54) METHOD OF MANUFACTURING A SHAPED TITANIUM ARTICLE

(75) Inventor: Michael R. Nowaczyk, Somerset, WI (US)

(73) Assignee: Greatbatch-Globe Tool, Inc., Minneapolis, MN (US)

( * ) Notice: Subject to any disclaimer, the term of this patent is extended or adjusted under 35 U.S.C. 154(b) by 209 days.

(21) Appl. No.: 10/936,755

(22) Filed: Sep. 8, 2004

(65) Prior Publication Data
US 2005/0055820 A1 Mar. 17, 2005

Related U.S. Application Data

(60) Provisional application No. 60/503,337, filed on Sep. 15, 2003.

(51) Int. Cl.
B21C 37/30 (2006.01)
B21C 1/00 (2006.01)
C21D 7/06 (2006.01)

(52) U.S. Cl. .............................. 29/90.7; 72/53; 72/340; 72/700; 148/670; 428/542.8; 623/901

(58) Field of Classification Search ................. 29/90.7, 29/557; 72/39, 40, 53, 274, 276, 340, 341, 72/700, 379.2; 148/669, 670, 559, 577; 428/542.8, 428/543; 623/901
See application file for complete search history.

(56) References Cited

U.S. PATENT DOCUMENTS

| | | | |
|---|---|---|---|
| 2,369,596 A | * | 2/1945 | Millen .......................... 148/243 |
| 3,309,906 A | * | 3/1967 | Bernick et al. ................. 72/47 |
| 4,077,811 A | | 3/1978 | Burman |
| 4,250,726 A | | 2/1981 | Safian et al. |
| 4,550,487 A | | 11/1985 | Hoshino et al. |
| 5,113,681 A | | 5/1992 | Guesnon et al. |
| 5,673,473 A | | 10/1997 | Johnson et al. |
| 2001/0003627 A1 | * | 6/2001 | Amamoto .................... 428/606 |

FOREIGN PATENT DOCUMENTS

| JP | 57160515 A | * | 10/1982 |
|---|---|---|---|
| JP | 01273609 A | * | 11/1989 |
| JP | 02059110 A | * | 2/1990 |

* cited by examiner

Primary Examiner—Jermie E. Cozart
(74) Attorney, Agent, or Firm—Michael F. Scalise

(57) ABSTRACT

A method of manufacturing a metallic blank into a shaped article useful as an enclosure for an implantable medical device is described. The method entails a plurality of steps in a particular order to obtain certain finish characteristics. Some of them are a surface roughness for bond ability and/or a uniform surface finish on the drawn section of the blank. The preset steps must be completed in a particular order; otherwise the desired characteristics are not provided.

16 Claims, 1 Drawing Sheet

METHOD OF MANUFACTURING A SHAPED TITANIUM ARTICLE

CROSS REFERENCE TO RELATED APPLICATION

The present application claims priority to U.S. provisional application Ser. No. 60/503,337, filed Sep. 15, 2003.

BACKGROUND OF THE INVENTION

1. Field of the Invention

The present invention is directed to processing a metal substrate intended for use as a medical device enclosure.

2. Prior Art

U.S. Pat. No. 5,673,473 to Johnson et al. relates to a "method of forming an implantable electronic device having shield portions that are formed after the finishing by a bead-blasting step and joining the shield portions to form a hermetic enclosure containing the electronic circuit." (See the examiner's reasons for allowance dated Feb. 26, 1997; underline added for emphasis.) In other words, the claims of the '473 patent are directed and limited to drawing and forming a metal shield AFTER beading blasting the metal. Moreover, Johnson et al. assert at column 1, lines 56 to 59 that their invention "performs the process steps on a continuous roll of titanium sheet stock, prior to forming, eliminating the need for subsequent processing steps."

In addition to disclosing its explicit method for surface finishing an enclosure for an implantable medical device, Johnson et al. refer to the prior art of U.S. Pat. No. 5,113,681 to Guesnon et al. This patent discloses a conventional "process and apparatus for forming a sheet element with contoured surface from a plane titanium alloy sheet by hot deep drawing process." Guesnon et al. describe their process at column 1, line 50 to column 2, line 28 as one "for fabricating contoured-surface sheet elements, particularly cylindrical or conical, that is simpler and faster and which nonetheless produces elements of regular thickness and precise dimensions with no cracks. The forming process . . . is characterized by the plane sheet element being preheated to a temperature of at least 730° C., by the preheated element being transferred to a non-preheated deep-drawing tool placed in the press soon enough for the temperature of the element to be still at least 700° C. at the time of the deep-drawing operation, by transferring the deep-drawn element to a calibration tool and heating the deep drawn element to at least 650° C. for a sufficient time for its definitive shaping, then allowing the so-processed element to cool to room temperature. The process of the present invention is particularly suitable for forming a sheet element 25 mm thick or less, and the deep-drawn element is preferably kept at a temperature of at least 650° C. in the calibration tool for at least one hour."

"For forming such a sheet element . . . the temperature of the deep-drawn sheet element is brought to about 650° C. in at least 5 hours and held at about 650° C. for approximately one hour, allowed to cool in the calibration tool for at least 10 hours, and then is removed from this tool and allowed to air-cool."

"The formed sheet element may . . . be descaled by shot-blasting and, for this purpose, steel balls with diameters between 0.6 millimeters and 0.16 millimeters are used for shot-blasting."

"After shot-blasting . . . the element is finished by being pickled in a cold bath of an aqueous solution with 15 to 40 wt. % nitric acid and 1 to 2 wt. % hydrofluoric acid, with the nitric acid/hydrofluoric acid weight ratio being higher than 10 and the solution containing less than 10 g/l of the total (iron+titanium) for 1 to 5 minutes followed by rinsing and drying."

"If, after forming, blasting, and the finishing stage of chemical pickling, the element is left in storage for a relatively long period of time, a patina forms which negatively affects its appearance but not its properties. It can then be chemically pickled in a cold bath similarly to the finishing stage of chemical pickling."

Johnson et al. found Guesnon et al.'s process and other conventional processes deficient for conditioning the metal in the roll form or after the rolling process at the mill. In particular, Johnson et al. state at column 1, lines 33 to 53 that:

"Surface finishing and bead-blasting of implantable medical device enclosures in particular, however, has traditionally been performed during the device enclosure manufacturing process subsequent to formation of the device enclosure itself. This is because suppliers of titanium have been unwilling to invest in additional specialized processing equipment necessary for bead-blasting material in the small quantities generally required by implantable medical device manufacturers. Another reason that surface finishing of implantable medical device enclosures has traditionally been performed at the finished device level is to eliminate any scratches or blemishes that have marred the device enclosure at earlier points in the enclosure manufacturing process. Therefore, while the surface finishing processes employed in the manufacture of titanium implantable medical device enclosures have been generally successful in providing devices having scratch-free surfaces, it is desired to develop a material finishing process that maintains a blemish-free surface while eliminating the necessity for the post-forming finishing processes normally associated with manufacturing of implantable medical device enclosures."

While the formed metal materials of the Johnson et al. and Guesnon et al. patents are completely acceptable for use as medical device enclosures, there is still a need for a drawn metal article having a uniform surface finish and with a sufficient surface roughness for bond ability during subsequent assembly operations. The present invention provides this.

SUMMARY OF THE INVENTION

The present invention is directed to a method of manufacturing a shaped metal article. The method entails a plurality of steps performed in a particular order to obtain desired finished characteristics. These include a surface roughness for subsequent bond ability and/or a uniform surface finish on the drawn section of the metal article. The present steps must be completed in a particular order; otherwise the desired objectives are unattainable.

In that respect, the present invention is directed to a method of manufacturing a shaped metal article, comprising the steps of: providing a blank of metal having at least an exterior surface and an interior surface; drawing the blank into a desired geometry of the shaped article; bead-blasting at least the exterior surface of the shaped article; drawing the shaped article at least a second time to a further desired geometry of the shaped article; and finishing the shaped article to the final desired geometry, wherein the final geometrically shaped article has a uniform surface finish on the drawn section of the metal.

These and other objects of the present invention will become increasingly more apparent to those skilled in the art

DETAILED DESCRIPTION OF THE INVENTION

Figure 1:
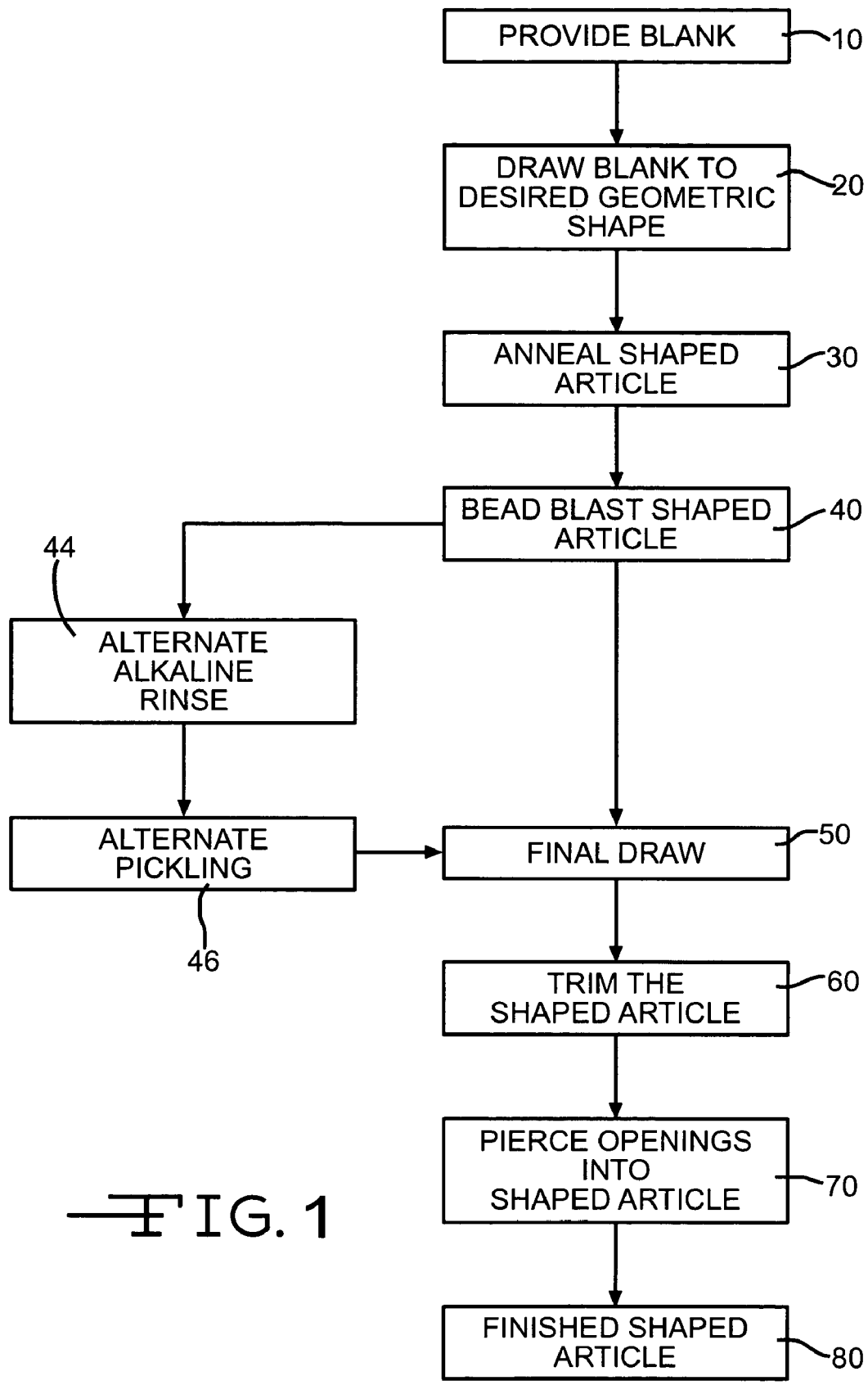
FIG. 1 is a flow chart of the present process for manufacturing a shaped article.

An object of the present invention is to provide a uniform surface finish on a drawn or shaped metallic article, and secondly, to improve the surface roughness of the metallic surface of the article for bond ability during subsequent assembly operations. None of the present process steps is unknown to those skilled in the art. Instead, it is their specific order that differentiates them from prior art processes for fabricating shaped metal articles for medical enclosure applications.

Referring now to FIG. 1, the steps for surface finishing a titanium substrate in accordance with the present invention are diagrammatically illustrated. Block 10 represents the first step of providing a blank, generally planar piece of titanium, which has been set to a desired thickness, and then drawing 20 the metal substrate into the desired geometrical shape of the article. Drawing consists of forcing the planar blank through an opening in a die. In this way, for example, a half shield can be formed from the planar blank. After the first drawing step 20, the shaped article is subject to an annealing process represented by block 30. The annealing process is by any conventional method known to those of ordinary skill in the art as suitable for use with titanium.

Block 40 represents the next step of treating the titanium article with bead-blasting media, preferably using ceramic or stainless steel beads. This step involves air blasting some or all of the titanium article with beads of a uniform size, or alternatively, nearly uniformly sized. A preferred ceramic bead is a fused zirconium silica material commercially available from S.E.P.R.-Les Miroirs-Cedex30, 92096 Paris La Defense, France. The size is B125, which has a nominal diameter of about 0.001 to about 0.005 inches. This material is comprised of, by weight: about 67% $ZrO_2$, about 30% $SiO_2$ (as an amorphous glassy phase devoid of crystalline silica), remainder being about 3% of a combination of $Al_2O_3$, $Fe_2O_3$, and $TiO_2$. Bead blasting with these materials leaves a surface finish having a satin appearance to the human eye. It is noteworthy that the combination of the titanium substrate and the 0.001 to 0.005 inch diameter ceramic or stainless steel beads does not leave any foreign matter embedded in the shaped article. Blasting with a fluid media, such as water, carrying either the stainless steel or ceramic beads, or a combination thereof, is an alternated method for treating the titanium article.

Block 44 represents an alternative alkaline rinse designed to remove organic contaminates residing on the titanium surface. Block 46 represents another alternative step of pickling the titanium article in an acidic solution in accordance with conventional methods. The pickling process removes the oxide layer formed during the annealing step 30 and that may have been left after the bead-blasting step 40. In that respect, pickling helps clean the surface of the shaped article.

Block 50 depicts a second drawing step that further forms the article into its final geometrical shape.

Block 60 represents the step of trimming. Trimming is by conventional methods and is generally the final process step prior to using the shaped article as an enclosure component in the manufacture of an implantable medical device. In that manner, trimming helps shape the article for subsequent machining and welding operations.

Block 70 represents the alternative step of piercing holes into the geometrically shaped article. Conventional punching tools or other conventional methods can form the holes.

The geometrically shaped article is now finished after trimming and/or piercing for use as an enclosure for a cardiac pacemaker, a defibrillator, a cardiac defibrillator, a drug pump, a cochlear implant, a neurostimulator, and the like. This is represented by block 80.

It is appreciated that various modifications to the inventive concepts described herein may be apparent to those of ordinary skill in the art without departing from the spirit and scope of the present invention as defined by the appended claims.

What is claimed is:

1. A method of manufacturing a shaped titanium article, comprising the steps of:
   a) providing a blank of titanium having at least an exterior surface and an interior surface;
   b) drawing the titanium blank into a desired geometry of the shaped article;
   c) annealing the shaped article;
   d) blasting at least a portion of the exterior surface of the shaped article with a bead material directly impinging on the titanium in a bead-blasting step;
   e) drawing the bead-blasted titanium at least a second time to a further desired geometry of the shaped article; and
   f) finishing the shaped article to a final desired geometry, wherein the exterior surface of the finished shaped article has a uniform surface finish on those portions that were bead-blasted and then drawn.

2. The method of claim 1 including trimming the shaped article after the second drawing step.

3. The method of claim 1 including pickling the shaped article after the bead-blasting step.

4. The method of claim 1 including subjecting the shaped article to an alkaline rinse after the bead-blasting step.

5. The method of claim 4 including pickling the shaped article after the alkaline rinse step.

6. The method of claim 1 including piercing the shaped article to provide it with apertures.

7. The method of claim 1 including bead-blasting the shaped article with either stainless steel or ceramic beads.

8. The method of claim 1 including providing the bead material having a diameter of about 0.002 to about 0.005 inches.

9. The method of claim 1 including providing the bead material as a fused zirconium silica material comprised of, by weight: about 67% $ZrO_2$, about 30% $SiO_2$, remainder being about 3% of a combination of $Al_2O_3$, $Fe_2O_3$, and $TiO_2$.

10. The method of claim 1 including blasting the bead material at the shaped article using either air or water.

11. The method of claim 1 including utilizing the finished shaped article in an implantable medical device.

12. A method of manufacturing a shaped article of titanium, comprising the steps of:
   a) providing a blank of titanium having at least an exterior surface and an interior surface;
   b) drawing the titanium blank into a desired geometry of the shaped article;
   c) annealing the shaped article;

d) air blasting at least a portion of the exterior surface of the shaped article with ceramic beads directly impinging on the titanium;
e) drawing the bead blasted titanium at least a second time to a further desired geometry of the shaped article; and
f) finishing the shaped article to a final desired geometry.

13. The method of claim 12 including providing the ceramic beads as a fused zirconium silica material comprised of, by weight: about 67% $ZrO_2$, about 30% $SiO_2$, remainder being about 3% of a combination of $Al_2O_3$, $Fe_2O_3$, and $TiO_2$.

14. A method of manufacturing a shaped metal article, comprising the steps of:
   a) providing a blank of metal having at least an exterior surface and an interior surface;
   b) drawing the blank into a desired geometry of the shaped article;
   c) annealing the shaped article;
   d) blasting at least a portion of the exterior surface of the shaped article with a bead material in a bead-blasting step;
   e) drawing the shaped article at least a second time to a further desired geometry of the shaped article;
   f) trimming the shaped article after the second drawing step; and
   g) finishing the shaped article to the final desired geometry.

15. A method of manufacturing a shaped metal article, comprising the steps of:
   a) providing a blank of metal having at least an exterior surface and an interior surface;
   b) drawing the blank into a desired geometry of the shaped article;
   c) annealing the shaped article;
   d) blasting at least a portion of the exterior surface of the shaped article with a bead material in a bead-blasting step;
   e) drawing the shaped article at least a second time to a further desired geometry of the shaped article; and
   f) finishing the shaped article to the final desired geometry including piercing the shaped article to provide it with apertures.

16. A method of manufacturing a shaped metal article, comprising the steps of:
   a) providing a blank of metal having at least an exterior surface and an interior surface;
   b) drawing the blank into a desired geometry of the shaped article;
   c) annealing the shaped article;
   d) blasting at least a portion of the exterior surface of the shaped article with a bead material in a bead-blasting step;
   e) drawing the shaped article at least a second time to a further desired geometry of the shaped article;
   f) finishing the shaped article to the final desired geometry; and
   g) utilizing the finished shaped article in an implantable medical device.

* * * * *